US00PP13782P39

(12) United States Plant Patent
Zipperer, III

(10) Patent No.: US PP13,782 P3
(45) Date of Patent: May 6, 2003

(54) GLADIOLUS PLANT NAMED 'ALEXANDRA THE GREAT'

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 09/877,571

(22) Filed: Jun. 8, 2001

(65) Prior Publication Data

US 2002/0002722 P1 Jan. 3, 2002

(30) Foreign Application Priority Data

Jun. 9, 2000 (EP) ..... 2000/0888

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, filed Dec. 20, 2000, Zipperer, III.
U.S. patent application Ser. No. 09/742,726, filed Dec. 20, 2000, Zipperer, III.
U.S. patent application Ser. No. 09/877,572, filed Jun. 8, 2001, Zipperer, III.
U.S. patent application Ser. No. 09/877,573, filed Jun. 8, 2001, Zipperer, III.
U.S. patent application Ser. No. 09/877,574, filed Jun. 8, 2001, Zipperer, III.
U.S. patent application Ser. No. 09/877,575, filed Jun. 8, 2001, Zipperer, III.
U.S. patent application Ser. No. 09/918,662, filed Jul. 31, 2001, Zipperer, III.
U.S. patent application Ser. No. 09/918,660, filed Jul. 31, 2001, Zipperer, III.
U.S. patent application Ser. No. 09/918,663, filed Jul. 31, 2001, Zipperer, III.

*Primary Examiner*—Bruce R. Campell
*Assistant Examiner*—Anne Marie Grünberg
(74) *Attorney, Agent, or Firm*—Laura G. Barrow

(57) ABSTRACT

A new and distinct gladiolus variety of plant, designated 'Alexandra The Great', is shown and described. Compared to the 'T-200' variety, the 'Alexandra The Great' variety is 30 cm taller and will maintain two to three more flowers in open bloom. The variety is also able to maintain up to ten flowers in open bloom simultaneously, beginning with a tight cut stem.

3 Drawing Sheets

The present invention comprises a new and distinct variety of a *Gladiolus l.* referred to by the variety name 'Alexandra The Great.'

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed. (The provisional breeder's designation "38–11" was used in a related application for a Community plant variety right filed earlier in the European Union Community Plant Variety Office). The female parent was a white gladiolus variety named 'T200,' an unpatented released variety by Turk characterized in part by having a harvesting time similar to the 'White Friendship' variety, 16–18 florets, and lightweight stems. The male parent was a green gladiolus variety named 'T-815,' an unpatented variety characterized in part by having a long head, small blooms, and poor opening ability. The seeds were planted in Ft. Myers, Fla., and the selection of 'Alexandra The Great' variety was made in Spring 1988. Asexual reproduction of the 'Alexandra The Great' variety was achieved by collecting cormels from the first corm and growing said cormels to maturity in Ft. Myers, Fla. All subsequent asexual reproductions of the 'Alexandra The Great' variety remain true to the original variety type.

BOTANICAL DESCRIPTION

Figure 1:
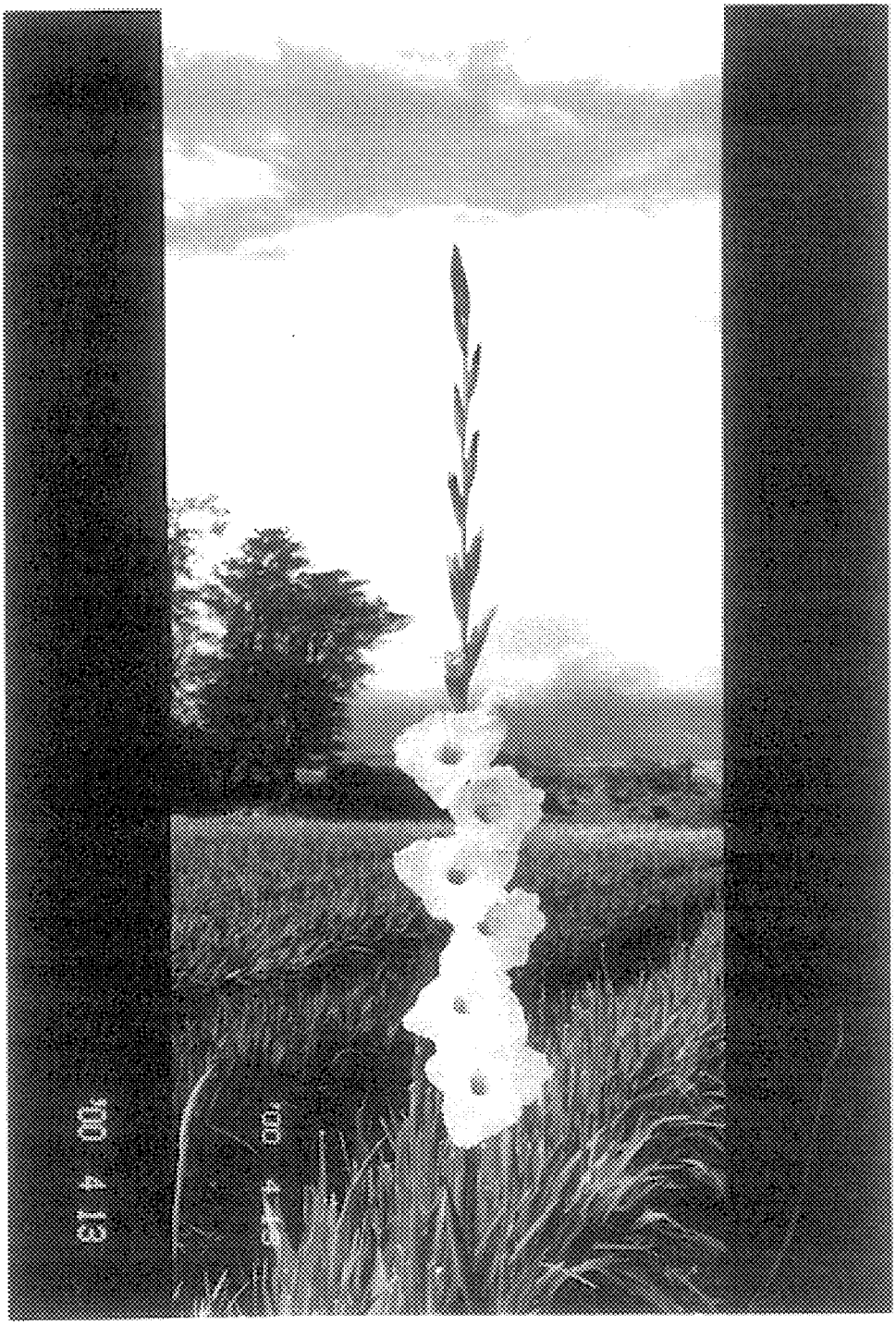
FIG. 1 is a photograph of a 'Alexandra The Great' variety plant in bloom.
Figure 2:
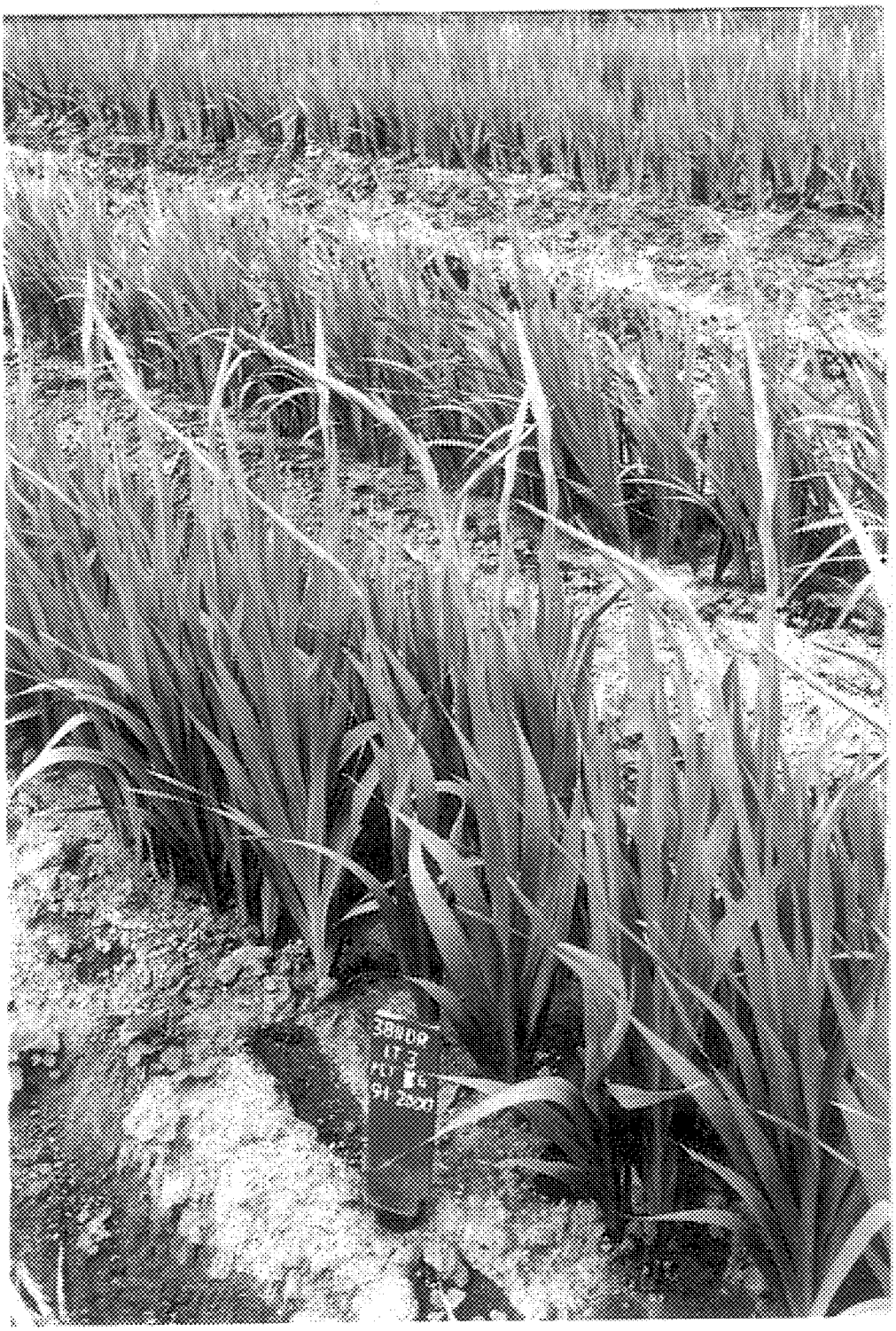
FIG. 2 is a photograph of the 'Alexandra The Great' variety plant prior to blooming.

The accompanying color photograph (FIG. 1) shows the inflorescence and various stages of blooming of the 'Alexandra The Great' variety plant.

The following botanical description, except for color, of the 'Alexandra the Great' variety was observed when the plant was 75 days old grown under the following conditions in Ecuador:

1) Twelve-hour daylight days with high light intensity;
2) Temperatures: 58–60° F. (low's) and 69–75° F. (high's);
3) Humidity: 50–55%
4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 143 cm and comprises 18–20 florets when grown from #1 size corms (1.5 inch) in Ecuador. The spike color is Yellow Green Group 144C on the back of the stem between the flower bud. The head length is about 60 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes). The leaf color of the 'Alexandra The Great' variety is Green Group 137C. The leaf size is about 67 cm (length) by 4 cm (width).

Figure 3:
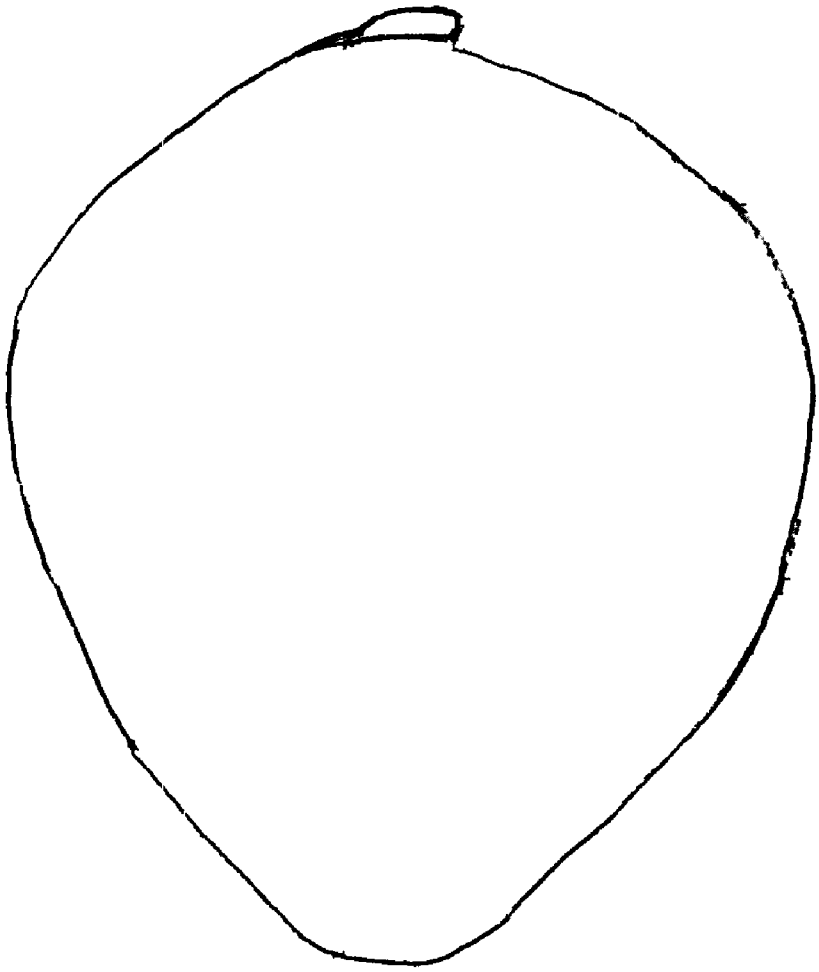
FIG. 3 is a drawing illustrating the shape of the petals.

The bud size of the 'Alexandra The Great' variety is about 7 cm in length. The flowers of the variety each consist of a total of six petals. Three large petals are oriented on the top half of the bloom and a medium-sized petal is oriented on the lower half of the bloom (at about 6:00). Two smaller petals are oriented on the lower half of the bloom adjacent to the lower medium-sized petal (i.e. at about 5:00 and 7:00). The shape of the large petals, as grown from a #3 corm, are best illustrated in FIG. 3, with dimensions of about 2.5 inches in width (at the widest point, then tapering down a shown) and about 2.75 inches in length. The diameter of the entire bloom is about 12 cm.

The color of the corolla bloom is a light green (i.e. Yellow Green Group 149D) deep inside the throat of the bloom and a uniform white color extending throughout the rest of the bloom. More specifically, the color of the tight bloom is Yellow White Group 158B. The color of the bloom in open perfect condition is White Group 155C. The color of the bloom open going down is also White Group 155C.

The flower also has one pistil and three stamens. The stamen stem is White Group N155A, and the stamen head has lines of Violet Group 86B on the pollen producing side. The back side of the stamen is Green White Group 157C. The pistil stem and pistil head are White Group 155C.

The corms of the 'Alexandra The Great' variety are typical for the gladiolus and have a Yellow Group 8A color under the husk on the top of the bulb one day after harvest.

GENERAL OBSERVATIONS

The 'Alexandra The Great' variety takes about 88 days to harvest in Ecuador, which is about 2–3 days faster than the Advance gladiolus variety. The variety of the present application performs well in all seasons times and tolerates high temperatures well without burning. The variety provides excellent growth in mid-winter days of 10.5 hours.

The variety usually produces one to two stems per Jumbo size corm (i.e. 1.75 inch in diameter and larger). The variety can maintain up to eight flowers in open bloom simultaneously in a vase of water and can be harvested with one flower showing color. The variety is an excellent opener after transport, in that the stems may be cut tight, shipped dry for a week, and still bloom well afterwards. The variety is also a fast opener.

The 'Alexandra The Great' variety is very resistant to attack by Fusarium fungi, and in fact, is more resistant to Fusarium than the 'T-200' parent variety; however, the variety is susceptible to Curvalaria fungi species. The 'Alexandra The Great' variety has a medium resistance to foliar diseases (slightly less than the 'T-200' variety).

The 'Alexandra the Great' variety does not emit a fragrance.

'Alexandra The Great' is most similar to its parent variety T-200. Compared to the T-200 parent variety, the 'Alexandra The Great' variety is 30 cm taller, produces three to four more florets per stem, has a bloom size that is about 1 cm wider in diameter, can hold two to three more blooms open, and is about two weeks slower to harvest. The 'Alexandra The Great' variety also has foliage that is a lighter green in color as well as heavier stem.

I claim:

1. A new and distinct gladiolus variety of plant named 'Alexandra The Great', as shown and described herein.

* * * * *